United States Patent [19]

Mathus

[11] Patent Number: 5,759,851
[45] Date of Patent: Jun. 2, 1998

[54] REVERSIBLE MEMBRANE INSERT FOR GROWING TISSUE CULTURES

[75] Inventor: Gregory Mathus, Concord, Mass.

[73] Assignee: Corning Incorporated

[21] Appl. No.: 510,852

[22] Filed: Aug. 3, 1995

[51] Int. Cl.[6] .................................................. C12M 3/00
[52] U.S. Cl. ............................... 435/297.1; 435/297.5; 435/305.1; 435/809.1
[58] Field of Search ............................ 435/297.1, 297.5, 435/809, 305.1

[56] References Cited

U.S. PATENT DOCUMENTS

| 4,142,940 | 3/1979 | Modolell et al. | 195/139 |
|---|---|---|---|
| 4,603,105 | 7/1986 | Kaplan | 435/7 |
| 5,139,951 | 8/1992 | Butz et al. | 435/284 |
| 5,272,083 | 12/1993 | Butz et al. | 435/240.241 |

FOREIGN PATENT DOCUMENTS 3938632  3/1991  Germany ..................... C12N 5/06

OTHER PUBLICATIONS

Patent Cooperation Treaty (PCT) Internation Preliminary Examination Report, International Application No. PCT/US96/12635, International Filing Date Feb. 8, 1996.

A Simple Approach to Measurement of Electrical Parameters of Cultured Epithelial Monolayers: Use in Assessing Neutropohil–Epithelial Interactions, James L. Madara et al., J. Tiss. Cult. Meth. 14:209–216.

An In Vitro Model for Cell–Cell Interactions, Kim B. Saunders and Patricia A. D'Amore, In Vitro Cell. Dev. Biol. 28A: 521–528.

*Primary Examiner*—David A. Redding
*Attorney, Agent, or Firm*—Wolf, Greenfield & Sacks, P.C.

[57] ABSTRACT

A device and method for growing tissue or cells on both sides of a membrane includes a cylindrical body which may be stood on either end in a culture well. A frame is slidably mounted in the body and carries a membrane, on both sides of which tissue or cells are to be grown. A tissue or cell sample is placed on the upper surface of the membrane and media is supplied to the well on the outside of the body. Passages at the bottom of the body allow the media to flow to the membrane and nurture the sample to cause its growth. When the first monolayer is grown, the body is inverted and the frame is pushed to the other end of the body, preferably by a jig supplied for that purpose. A second cell sample is deposited on the other side of the membrane, again on top of the membrane and it is nurtured by media supplied primarily from the reservoir on top and secondarily through the membrane.

32 Claims, 7 Drawing Sheets

REVERSIBLE MEMBRANE INSERT FOR GROWING TISSUE CULTURES

This invention relates to devices and methods for growing cells or tissue in vitro. More particularly, this invention relates to growing tissue, cells or cell lines on opposite faces of a sterile cell or tissue retention member submerged in tissue culture media and/or positioned at the media/air interface.

Laboratory research has a need to study cell-to-cell interactions in tissue culture with different cell populations separated by microporous membranes. Cell-to-cell interactions are believed to be important in the regulation of cellular growth and differentiation. During the process of embryonic determination cell-to-cell contact is essential for many cell types. Beyond embryological development, the growth and differentiation of many other cell types is also thought to be dependent on cell-to-cell interactions. For example, the differentiation of myoblasts into myotubes is believed to be dependent on the contact between the undifferentiated cells. Lymphocyte development and activation is likewise dependent on cell-to-cell contact. A wide variety of cell types and tissues are dependent on these cell-to-cell interactions.

Although it is unknown why cell-to-cell contact can cause changes in cellular development and differentiation of cells researchers are actively testing several hypotheses in hopes of answering this question. One hypothesis that has been proposed is that contact at the cell surface of one cell by another cell leads to changes in gene expression as a result of interaction with a surface receptor or other signaling mechanism. An alternate hypothesis that has been proposed is that one cell might produce a layer of extracellular matrix on its surface and that it is the extracellular matrix which actually contacts a second cell causing the subsequent changes in gene expression of the second cell. Alternatively, some researchers hypothesize that the cell-to-cell interaction is not so much dependent on the physical contact between the cells but rather the contact with factors which are produced by the cells and released into the external environment. Some cells produce factors which are capable of acting immediately in the local environment whereas other cells produce factors which are long lived and can be transported to distant sites in the body.

Various techniques are presently used for studying cell-to-cell interactions but none are wholly satisfactory because they require a great deal of manipulation with the attendant risk of contamination. In one technique a microporous membrane is floated in a pool of tissue culture media and a first cell type is grown on one face thereof. The membrane is then inverted and a second cell type is grown on the other face. The technique is not acceptable in many applications because it is important to totally isolate the cell culture and media on one face of the membrane from cell culture and media on the other face thereof.

A common technique used for studying cell-to-cell interaction in which the release of a factor by one set of cells causes a change in another set of cells, involves the use of conditioned media. Conditioned media is a media which has been incubated in the presence of a first set of cells for a time period long enough such that the cells have secreted factors into the media. A second set of cells is plated as a monolayer at a low density and then the sparsely plated monolayer of cells is incubated with the conditioned media to determine the effect of the factors on the cells. One problem with this method is the risk of contamination due to excessive manipulation and an extended period of incubation. Another problem is that some factors are only effective for very short periods of time (sometimes for only a matter of minutes) and thus need to be contacted with the effector cell immediately for any result. Short lived and unstable factors are very difficult if not impossible to study by using the traditional technique of conditioned media.

Another technique used in the past involves clamping a membrane between two plastic or metal rings and submerging the unit in media to a depth greater than the membrane. The first cell type is grown on the top surface, and the unit is then inverted and a second cell type is grown on the opposite face of the membrane. Difficulties are frequently encountered with this technique because the first grown cell type seals the microporous membrane, which creates an air lock and corresponding air bubble under the membrane and inside of the clamp ring when the unit is inverted to grow the second cell type. (An air bubble may kill the culture on the membrane or prevent transport studies from being properly performed.) To avoid this problem a hole and plug are sometimes provided in the side wall of the clamp so that the hole may be opened to let air escape and then be reclosed by the plug to maintain the isolation between the two cell types. This solution is not satisfactory because it is difficult to remove and replace the plug and maintain the essential sterile conditions, and it is also difficult to determine whether all the air has been removed.

An object of the present invention is to provide a method and apparatus for enabling a user to grow cells on both sides of a membrane under sterile conditions such that one can measure cell-to-cell interactions.

SUMMARY OF THE INVENTION

The present invention is embodied in an easy to manufacture assembly which includes a tubular body open at each end and which is capable of being stood on either end in a culture well. A frame sized to slidably fit within the tubular body carries a culture retention member such as a microporous cell or tissue retention member across its inner diameter and a seal about its outer diameter. The cell or tissue retention member includes a microporous membrane. The seal seals the frame against the inner surface of the body and prevents media from flowing about the frame ring from one side of the member to the other. The frame is positioned in the body adjacent one end thereof, and the body is stood on that end in the well. Media in the well submerses the lower portion of the body and both the top and bottom surfaces of the cell or tissue retention member, and cells are grown on the top surface. When a monolayer is achieved, the body is inverted and the frame is moved to the opposite end (the other end on which the body now stands). This allows cells to grow on the other side of the cell or tissue retention member.

In an embodiment of the invention a jig is provided. The jig is sized to fit within the body and engage the frame so that the jig will position the frame with its cell or tissue retention member at the desired distance from the end of the body on which the body stands. A stop mechanism is provided so that the frame is moved only to a precise position by the jig. In one embodiment, the stop mechanism is the jig provided in the form of a cylinder having a flange at one end which exceeds the diameter of the tubular body and at the other end having a cylinder which is sized to fit within the tubular body. In another embodiment the body has projections at one end, extending inwardly toward the center of the body, upon which the frame may rest. In this embodiment, the jig which fits within the tubular body so that it can engage the frame and move the frame into contact with the projections. This stop mechanism is provided so that the frame is moved into the proper position at the other end of the body.

In another embodiment of this invention, each end of the body has interruptions such as notches or feet which effectively raise the ends of the body off the surface of the well containing the media. This allows for media movement and media exchange under the cell or tissue retention member.

Yet another feature of the invention is that the frame supporting the cell or tissue retention member can be slid out of the body for use in other devices such as a perfusion chamber or be stored as a permanent record.

This invention is also useful for layered cell culture to study cell-to-cell interactions. This can be accomplished by growing cells on a first cell or tissue retention member (or different cells on both sides of a first cell or tissue retention member), placing additional frames with separate cell or tissue retention members in the body and growing monolayers on the additional cell or tissue retention members.

A further embodiment of the invention includes a kit for growing tissue and cells to study cell-to-cell interactions.

The invention will be better understood and appreciated from the following detailed description of an illustrative embodiment thereof shown in the accompanying drawings.

DETAILED DESCRIPTION

Figure 1:
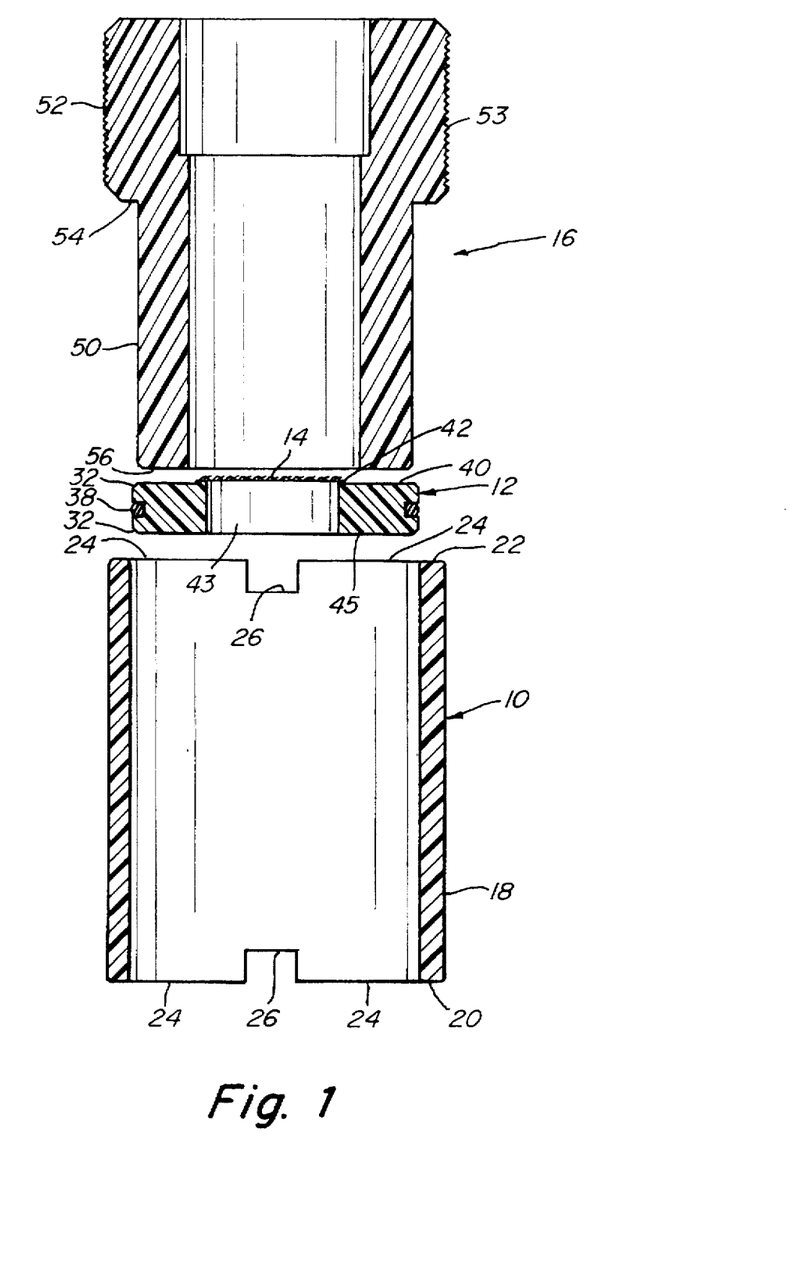
FIG. 1 is an exploded perspective view of an illustrative embodiment of a culture device constructed in accordance with this invention.
Figure 2:
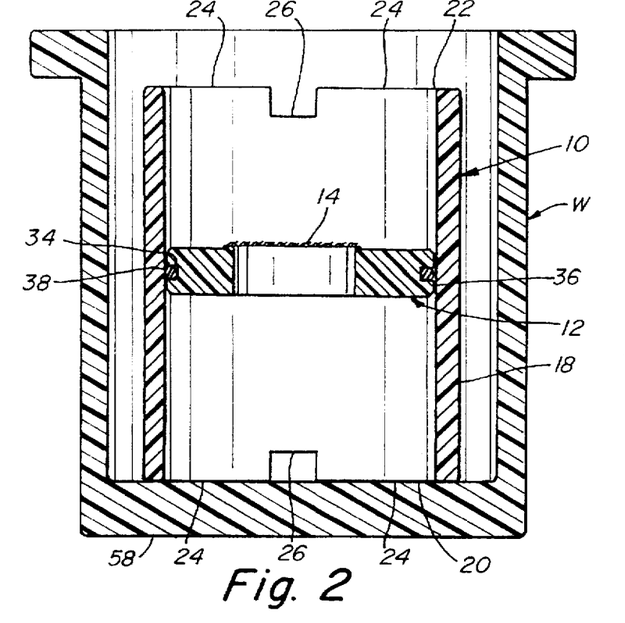
FIG. 2 is a cross-sectional elevation view of the body support and cell retention membrane with its carrying frame comprising part of the device shown in FIG. 1.

FIG. 1 illustrates a tissue or cell growth device in accordance with the present invention. The three major parts of the apparatus of the embodiment shown in FIG. 1 include tubular body 10, frame 12 with its cell retention member in the form of a multiporous membrane 14, and jig 16. The body 10 and frame 12 are assembled together when the device is used, while the jig is used to properly position the frame in the body so that the cell or tissue retention member is the desired distance above the bottom of the culture well, as is described more fully below.

Figure 4:
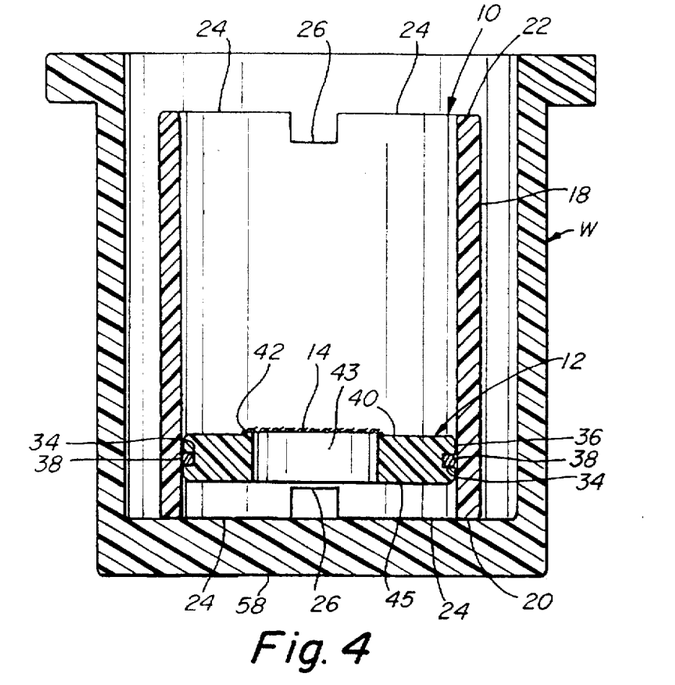
FIG. 4 is a cross-sectional view of the assembled body and frame with its cell or tissue retention member disposed in a culture well and suggesting the growth of cells on the upper surface of the cell or tissue retention member.

The body 10 is composed of a cylindrical side wall 18 and may be made of any material having sufficient strength to act as a liquid barrier. Examples of acceptable materials include thermoplastics (such as Styrene, Lexan, and polyesters) and aluminum. When a thermoplastic is used, the body 10 can be formed by conventional injection molding techniques. Each end 20 and 22 of the body has a support comprising a number of spaced apart feet 24 separated by notches 26. In the embodiment illustrated in the figures, three feet 24 are provided at each end, although only two are represented in the view shown. The feet are intended to support the body in a culture well W as shown in FIG. 4, and the notches 26 provide flow passages for media to pass from around the outside of the body 10 to the space below the frame 12 and cell or tissue retention member 14 and above the bottom wall 58 of well W as more fully described below in connection with the use of the device. The feet 24 at each end are capable of supporting the body vertically in the well with either end down, and in both positions the notches will allow media to enter the space below the frame 12 and the cell or tissue retention member 14 and above the well bottom wall.

The frame 12, which also may be made of a thermoplastic such as Styrene or some other material compatible with the test or experiment being conducted, has an outer diameter just small enough so that it may be slid conveniently into the body 10. The outer corners 32 of the frame 12 may be chamfered as suggested in the drawing to facilitate insertion of the frame in the body. An O-ring seat 34 is provided in the outer surface 36 of the frame 12 and carries an O-ring 38 that provides a seal about the frame to prevent the flow of a culture media upwardly from the bottom of the frame to its upper surface within the body 10 and by-passing the cell or tissue retention member 14. Other sealing methods may also be used. One side 40 of the frame carries a short platform 42 on which a cell or tissue retention member may be secured. The frame acts as a support which is slidable axially in the body. In the embodiment illustrated in the drawings, the body is essentially cylindrical and the frame is a circular ring.

The frame has a bore 43 in the center, extending from the first side 40 of the frame to the second side 45 of the frame. The bore may be essentially cylindrical. In another embodiment shown in FIG. 8A the bore 43a of the frame 12a is beveled such that the internal diameter of the bore on the first side 40a of the frame is smaller than the internal diameter of the bore on the second side 45a of the frame. The advantages of the beveled bore are described below.

The cell or tissue retention member 14 carried by the frame may be formed of any material capable of supporting cells or tissue substantially isolated from direct contact with media in the well, while allowing at least selected material to pass through and contact the cells. Such materials include microporous membranes, hydrated gels, ultrafiltration membranes, or layered combinations such as a gel supported on a screen. The cell or tissue retention member 14 may be a microporous, track-etched, or cast membrane and is attached to the frame 12 by heat sealing, solvent bonding, ultrasonic welding, clamping, or any other method which does not detrimentally affect the properties of the cell or tissue retention member or the growth of cells upon the cell or tissue retention member.

The cell or tissue retention member may optionally be treated to produce a variety of surfaces for cell attachment. Different cell types preferentially attach to different surfaces. Thus, by providing different surfaces for cell attachment, the process of cell attachment can be manipulated and studied, with different surfaces being utilized to study the binding properties of a particular cell type. For example, a particular cell type might bind to one type of integrin but not another. Thus by treating the surface of the cell retention member with different types of integrins, the identity of the integrin receptor expressed on the particular cell type being studied can be determined by identifying the type of integrin that the cell interacts with.

The treated surfaces of the cell retention member may interact with a particular cell type to either cause the cell to attach to the surface, or to prevent the cell from attaching. The cell retention member surface may be treated by exposing the surface to a composition having the desired cell attachment properties. As used herein, the term cell attachment properties includes any property of a composition that causes a cell to adhere to the composition or prevents a cell from adhering to the composition. Examples of compositions which may be used include, but are not limited to, extracellular matrix proteins, integrins, and antibodies. Extracellular matrix proteins may be natural or synthetic. Natural extracellular matrix proteins include for example collagen, laminin, and fibronectin. Synthetic extracellular matrix proteins include synthetic analogs and defined peptides.

A treated surface may also be advantageous in isolating a single cell type from a tissue sample which contains a mixture of cell types. Often it is desirable to isolate one cell type from the others within a mixed tissue sample. If the desired cell type has different binding properties than those with which it is mixed, the surface of the cell retention member can be manipulated so that it selectively binds to the desired cell type but not the others.

The surface of the cell retention member may also be treated to enhance cell binding generally, such that any cell type will bind preferentially to the cell or tissue retention member rather than other parts of the device. This can be accomplished by treating the cell or tissue retention member to provide a hydrophilic surface, i.e., by chemical or plasma treatment.

The cell retention member can also be divided into regions, with each region being treated with a different compound to produce multiple cell attachment surfaces on the cell retention member such that each region attracts a different type of cell.

Figure 3:
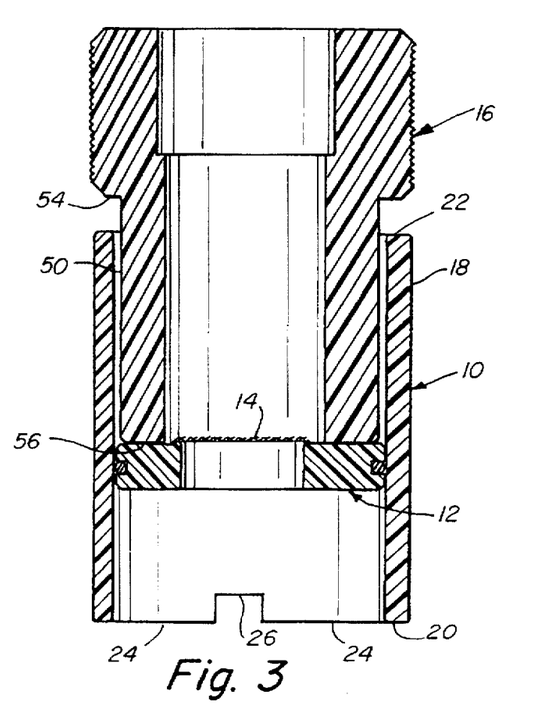
FIG. 3 is a cross-sectional view similar to FIG. 2 but showing the jig being used with the assembled parts to position the cell or tissue retention member within the body.

The jig 16 may also be molded of a thermoplastic such as Styrene like the other parts of the device. In one embodiment, the jig includes a plunger 50 and handle or flange is 52 having a knurled outer surface 53. The handle or flange has a diameter larger than the inner diameter of the body 10, and in the form shown it is larger than the outer diameter of the body as well. The bottom of the handle 52 defines a shoulder 54 that engages the end of the body through which the plunger 50 is inserted to orient the frame 12 and its cell or tissue retention member 14 in the body. The outer diameter of the plunger 50 is slightly less than the inner diameter of the body 10 so that it can be inserted into the body and engage the frame 12 and push it axially in the body to the position desired. The inner diameter of the plunger preferably is greater than the diameter of the plat-form 42 so that the end 56 of the plunger will not engage the cell or tissue retention member 14 attached to the frame when the jig is inserted into the body 10 to position the frame and its cell or tissue retention member. This relationship is clearly shown in FIG. 3.

Figure 9:
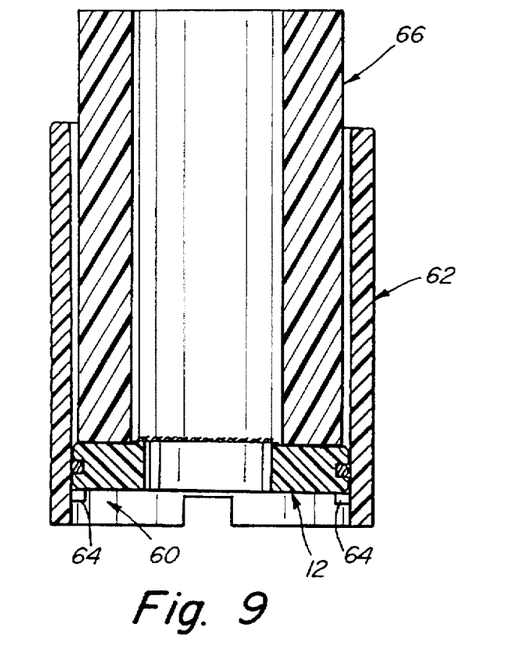
FIG. 9 is a cross-sectional view of another embodiment of body and jig constructed in accordance with this invention.

In another embodiment shown in FIG. 9 a stop 60 is provided in which the body 62 has projections 64 at one end extending inwardly toward the center of the body, upon which the frame 12 may rest. In this embodiment, the jig 66 has a shape which fits within the tubular body so that it can engage the frame and move it into contact with the projection 64 at the other end of the body 62. This stop mechanism 60 is provided so that the frame is moved only to a precise position by the jig.

In FIGS. 4–7, a use of the device for growing cells or tissue on both sides of the cell or tissue retention member is illustrated. In FIG.4, the assembly made up of the body 10, frame 12 and cell or tissue retention member 14 is shown standing in the well W with the feet 24 on the end 20 of the body engaging the well bottom wall 58. The frame 12 is oriented with the cell or tissue retention member 14 on the upper side of the frame (on side 40), and the frame is disposed adjacent the lower end 20 of the body. The precise position of the frame may be established with the use of jig 16. A cell or tissue sample is attached to the upper surface of the cell or tissue retention member 14, and culture is medium is supplied to the well W on the outside of the body. Care should be taken to supply the medium only on the outside of the body in order to minimize the possibility of air entrapment on the underside of the cell or tissue retention member 14. The medium will flow through the notches 26 between the legs 24 on which the body stands and wet the underside of the cell or tissue retention member. Once the cell or tissue retention member is wet, additional medium and the cells are deposited on the upper surface of the member. The cells will be nurtured by the medium reaching it both through the cell or tissue retention member 14 as well as by the medium above the cell or tissue retention member. This closely mimics the conditions in normal cells and tissue grown in living bodies.

Figure 8A:
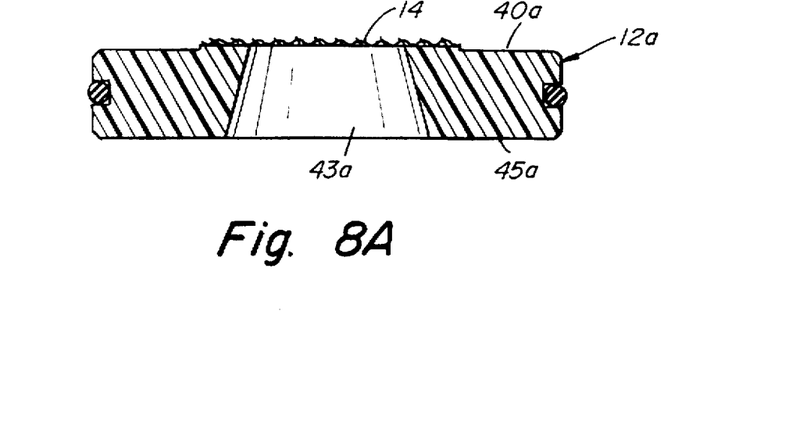
FIG. 8A is an enlarged cross-sectional view of a second embodiment of a frame and cell retention member.
Figure 8B:
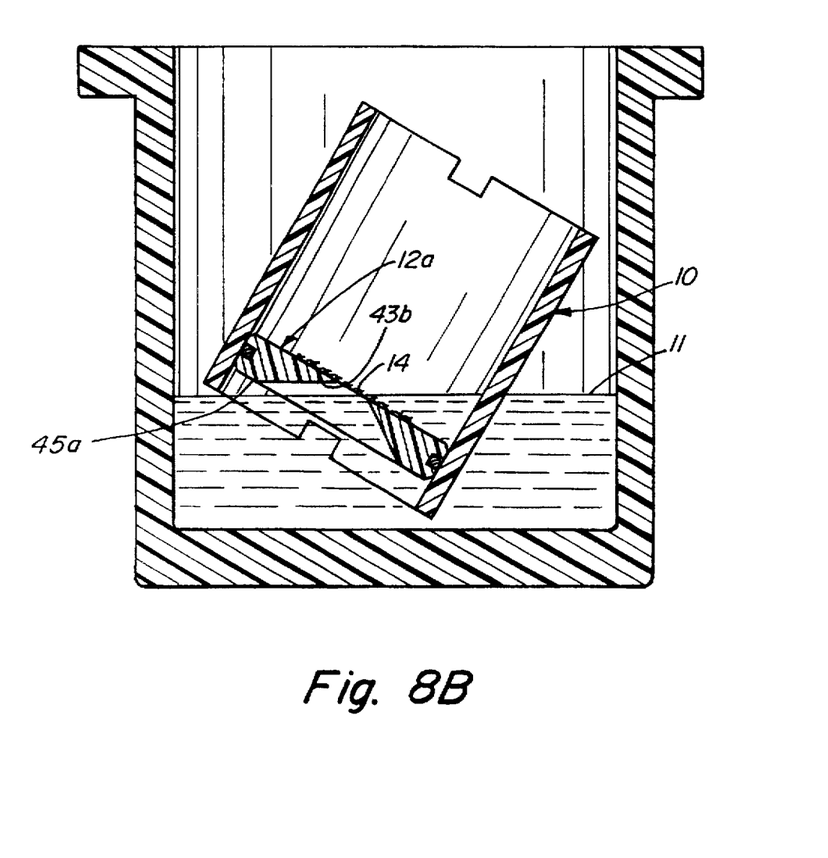
FIG. 8B is a diagrammatic view of the body and support illustrating the benefit desired from the embodiment of FIG. 8A.

When the bore is beveled as shown in FIG. 8A at 43a and 43b, the tissue or cell growth device may be placed into a well containing culture medium with minimal air entrapment. If the device is lowered into the culture medium at an angle such that the beveled wall of the bore 43b is substantially parallel with the surface of the culture medium 11 then the air may escape and avoid becoming entrapped under the cell or tissue retention member. This is suggested in the diagrammatic view of FIG. 8B.

Figure 5:
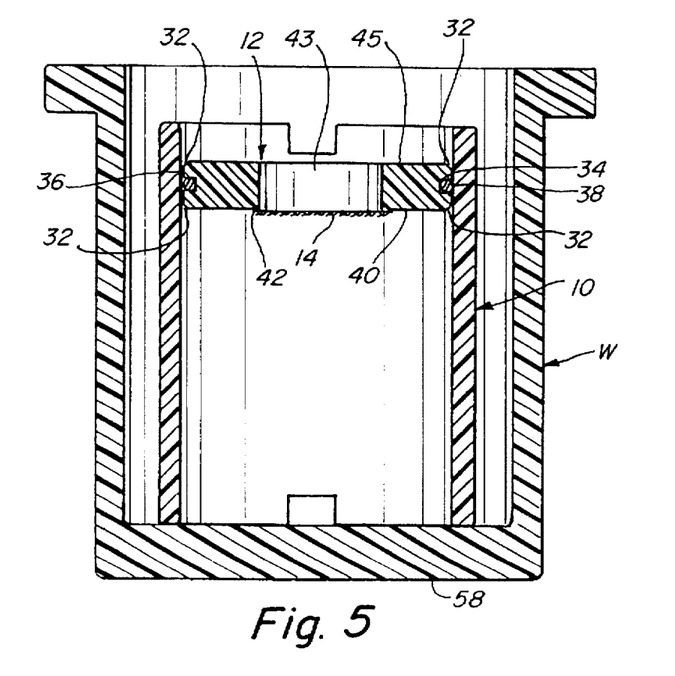
FIG. 5 is a cross-sectional view similar to FIG. 4 and showing the body inverted in the culture well.
Figure 6:
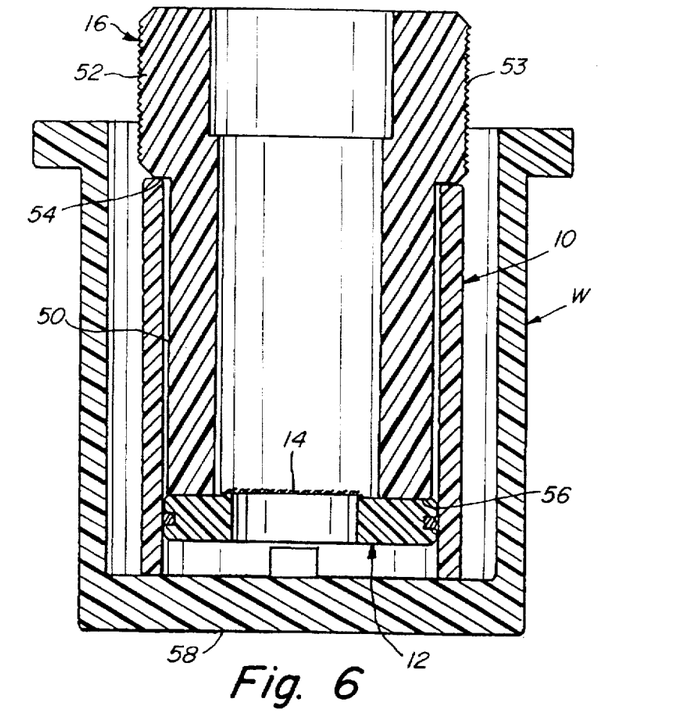
FIG. 6 is a cross-sectional view similar to FIG. 5 but showing how the jig is used to position the frame and the cell or tissue retention member in the desired position for growing cells on the opposite side of the cell or tissue retention member.
Figure 7:
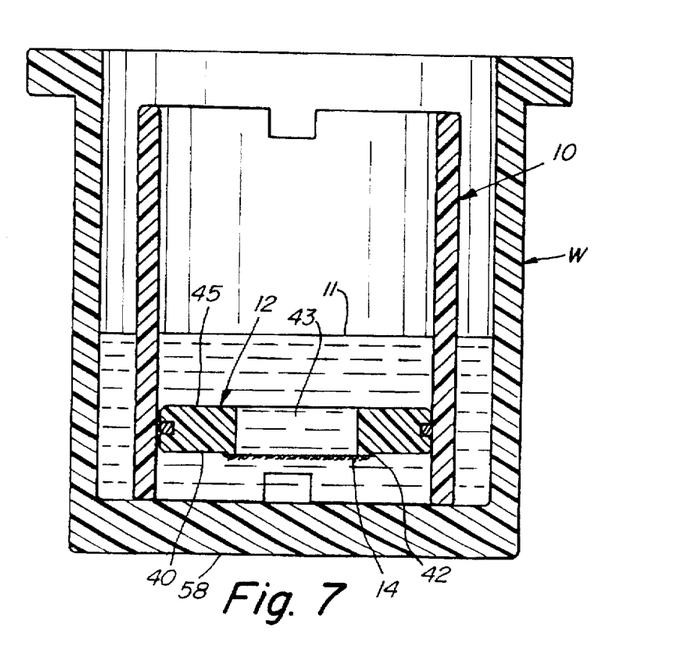
FIG. 7 is a cross-sectional view showing the second cell type growing on the opposite side of the cell or tissue retention member.

Once the cells are established, the body 10 with the frame and cell or tissue retention member is inverted in the well W (or it may be placed in a new well), and the frame is moved to the lower end of the body as suggested in FIGS. 5 and 6. The jig 16 is used to precisely position the frame 12. The length of the plunger 50 measured from the shoulder 54 to the end 56 is selected to achieve the frame position desired. After the jig is removed, a second sample is applied to the new upper surface of the cell or tissue retention member, and additional medium may be supplied to the well. The sample on the new upper surface is primarily nurtured from the cell or tissue retention member. This layering of two cell types separated by a cell or tissue retention member simulates conditions seen in vivo.

In one embodiment of the invention, the likelihood of air bubbles being entrapped under the member is minimized by positioning the cell or tissue retention member on one side of the frame. The cells should be attached first to the side of the cell or tissue retention member facing away from the bore of the frame. When the member is in the position such that the member is above the bore of the frame, and media is added from the underside of the member before the addition of the cells, the entrapment of air bubbles will be minimized as a result of the air escaping through the dry member. After the first set of cells form a monolayer on the retention member, the device can be inverted so that the surface of the cell or tissue retention member positioned toward the bore is facing upwardly, and a second set of cells can be plated on this surface. In the inverted orientation the frame and the surface of the cell or tissue retention member form a flat surface without a bore. When the flat surface of the cell retention member is slid by the jig into a position where it is level with the notches on the body, air entrapment under the cell retention member is prevented because the air can escape through the notches.

As used herein, the term cells is intended to include any type of cell, for example, established cell lines, primary culture cells, and isolated tissue. Thus, reference to a device or member for growing or retaining cells is intended to indicate a device for use with any such cell or tissue.

Many cell-to-cell interactions may be studied using the tissue or cell growth device and method of the invention. A cell-to-cell interaction is a contact between a first cell and a second cell. Cell-to-cell interactions may be direct or indirect. A direct cell-to-cell interaction is one in which the surface of the first cell comes into direct contact with the surface of the second cell. Direct cell-to-cell interaction may involve transmigration of the cells, that is, cell movement. An indirect cell-to-cell interaction is one in which the first cell comes into contact with the factors produced and released by the second cell. The is surface of the cell includes the cell membrane, any surface receptors or other proteins, and any extracellular matrix which has been produced by the cell and layered on its surface.

The pores of the cell or tissue retention member have a diameter such that cell-to-cell interactions can occur. The diameter of the pores depends upon the particular interaction to be studied and could readily be determined by one of ordinary skill in the art.

Once different cell types have been grown on opposites sides of the membrane, the effects of the cell-to-cell interactions may be studied. The frame may be removed from the body and treated or stored as desired. One mechanism by which the cells can be studied is by electron microscopy.

The device and method of the invention may also be utilized to study cellular migration. A monolayer of cells may be plated on one side of the membrane and then a second cell type may be layered on top of the first cell type. Migration may then be determined by removing the cell or tissue retention member and determining the positions of the cells.

Figure 10:
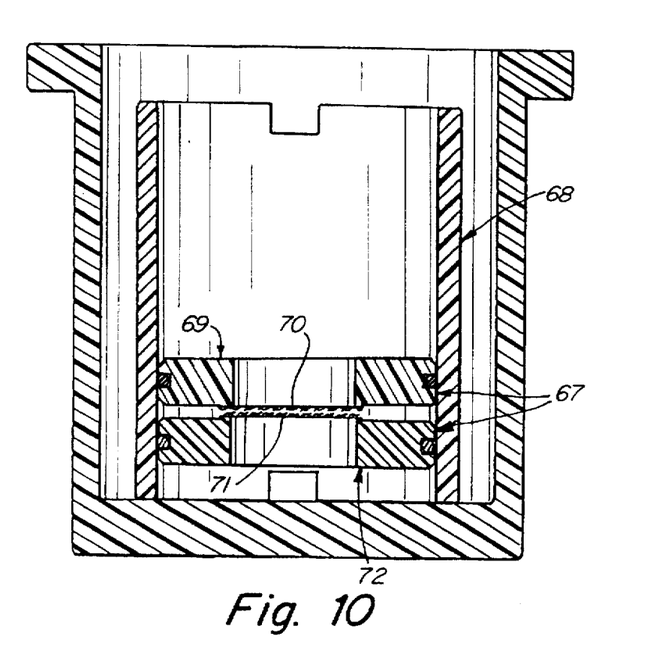
FIG. 10 is a cross-sectional view of a plurality of frames in the body.
Figure 11:
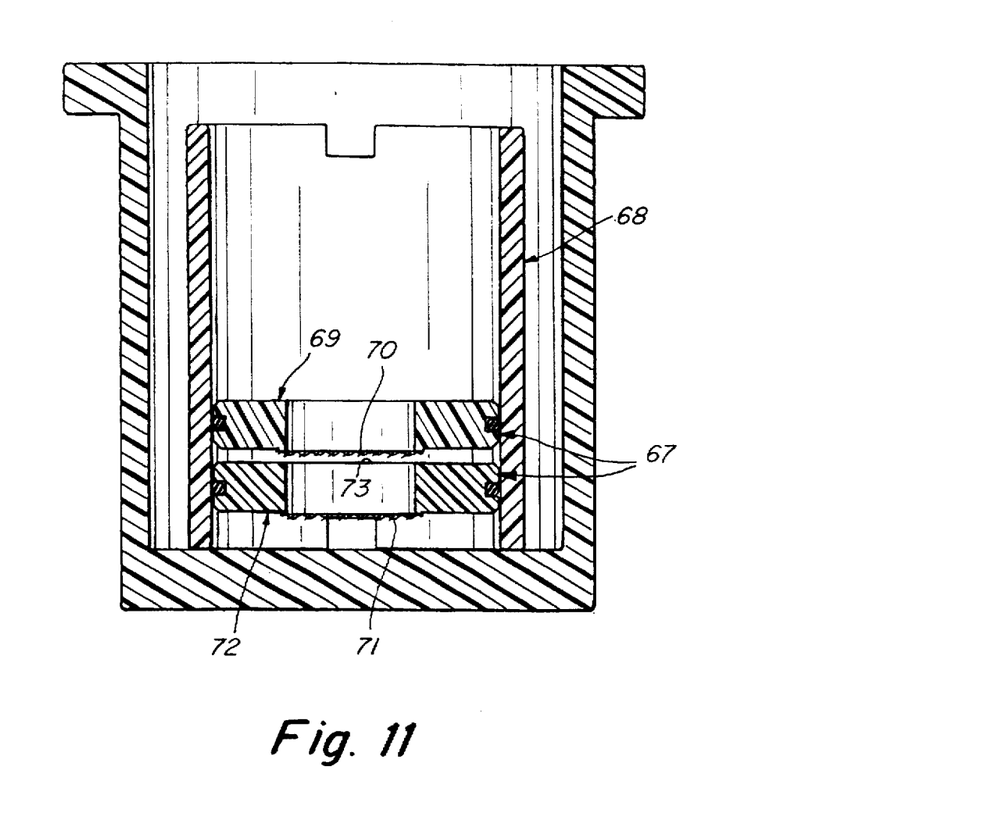
FIG. 11 is a cross-sectional view of a plurality of frames in an alternate orientation within the body.

The tissue or cell growth method and apparatus of the present invention may be used with a single frame 12 as discussed above, or may be used with multiple frames 67 as shown in FIGS. 10 and 11. The maximum number of frames 67 that may be used is that number of frames which have a combined height which is equal to or less than the height of the body 68 and is determined by the height of the individual frames used. The frames 67 may be positioned within the body 68 such that the cell or tissue retention member of one frame is in various orientations with respect to the cell or tissue retention member of the other frames. The cell or tissue retention member 70 of the first frame 69 may be adjacent to the cell or tissue retention member 71 of the second frame 72. FIG. 10, or alternatively as shown in FIG. 11, it may be adjacent to the other end 73 of the second frame 72 such that the cell or tissue retention members 70 and 71 of the two frames are separated by a distance equivalent to the height of one frame.

In another embodiment a kit for growing tissue or cells in a culture well is provided. The kit includes a tubular body and at least a first frame which fits within the body and has a cell or tissue retention member having a plurality of pores. The pores of the cell or tissue retention member have a diameter such that cell-to-cell interactions can occur. The diameter of the pores depends upon the particular interaction to be studied and could readily be determined by one of ordinary skill in the art.

Optionally the kit may also contain an electron microscopy buffer assay system. An electron microscopy buffer assay system includes the buffers necessary to perform electron microscopy on a cell or tissue retention member on which cells have been grown and the particular components are well known to those of ordinary skill in the art. For example the reagents may include phosphate buffered saline (PBS), paraformaldehyde/glutaraldehyde in cacodylate buffer, osmium tetroxide, and a graded series of ethanol.

From the foregoing description, those skilled in the art will appreciate the many advantages of this invention and will also appreciate that modifications may be made of the illustrative embodiments without departing from the spirit of the invention. Therefore, it is not intended that the scope of the invention be limited to the specific form shown and described, but rather its breadth is to be determined by the appended claims and their equivalents.

I claim:

1. A cell growth device for placement within a culture well, comprising:

a body having an opening at a first end and at a second end, and an inner surface defining a lumen extending between the openings at the first and the second end;

at least one frame having an outer surface which is slidably mountable within the lumen, the at least one frame having a first side and a second side;

a seal operatively connected between the at least one frame and the inner surface of the body to prevent a flow of a culture media between the at least one frame and the inner surface of the body; and a cell retention member secured to the first side of the at least one frame for retaining cells; wherein the at least one frame with the cell retention member secured thereto is constructed and arranged for movement in the lumen between a first position and a second position.

2. The device as defined in claim 1, wherein the first position is adjacent the opening at the first end of the body and the second position is adjacent the opening at the second end of the body.

3. The device as defined in claim 2, wherein the body has a first support at a first end and a second support at a second end, the first and second supports each being adapted to support the cell growth device so that it can stand on either of the first and second ends in the culture well.

4. The device as defined in claim 2, further comprising a jig having a plunger adapted to be received in the lumen and to engage the at least one frame so that the at least one frame can be slidably positioned with respect to the openings at the first and second ends of the body.

5. The device as defined in claim 1, wherein the body has a first support at a first end and a second support at a second end, the first and second supports each being adapted to support the cell growth device so that it can stand on either of the first and second ends in the culture well.

6. The device as defined in claim 5, wherein the first and second supports each have at least one opening that communicate with the lumen.

7. The device as defined in claim 5, further comprising a jig having a plunger adapted to be received in the lumen and to engage the at least one frame so that the at least one frame can be slidably positioned with respect to the openings at the first and second ends of the body.

8. The device as defined in claim 5, wherein the at least one frame has an inner surface that defines a bore extending from a first opening on the first side of the at least one frame to a second opening on the second side of the at least one frame, and wherein the cell retention member is disposed at least partially across the first opening.

9. The device as defined in claim 1, further comprising a jig having a plunger adapted to be received in the lumen and to engage the at least one frame so that the at least one frame can be slidably positioned within the body.

10. The device as defined in claim 9, further comprising a stop disposed in the lumen of the body and adapted to engage the at least one frame and prevent the at least one frame from being slid beyond the stop.

11. The device as defined in claim 9, wherein a distal tip of the plunger includes a rim defining a cavity having a diameter greater than a diameter of the cell retention member.

12. The device as defined in claim 1, wherein the lumen is cylindrical and the at least one frame is a ring.

13. The device as defined in claim 1, wherein the at least one frame, the cell retention member and the seal divide the lumen into two separate fluid compartments.

14. The device as defined in claim 13, wherein the seal and the cell retention member prevent cells from passing from one of the two separate fluid compartments to the other.

15. The device as defined in claim 1, wherein the at least one frame has an inner surface that defines a bore extending from a first opening on the first side of the at least one frame to a second opening on the second side of the at least one frame so that the cell retention member is disposed at least partially across the first opening.

16. The device as defined in claim 15, wherein the bore is beveled.

17. The device as defined in claim 16, wherein the bore has a diameter on the first side of the at least one frame that is smaller than a diameter of the bore on the second side of the at least one frame.

18. The device as defined in claim 1, wherein the cell retention member is hydrophilic.

19. The device as defined in claim 1, wherein a height of the at least one frame is substantially less than a height of the body.

20. The device as defined in claim 1, wherein the at least one frame includes first and second frames.

21. The device as defined in claim 20, wherein the second frame is oriented so that the first side of the second frame is positioned adjacent the first side of the first frame.

22. The device as defined in claim 20, wherein the second frame is oriented so that the first side of the second frame is positioned adjacent the second side of the first frame.

23. The device as defined in claim 20, wherein the second frame is oriented so that the second side of the second frame is positioned adjacent the second side of the first frame.

24. The device as defined in claim 1, wherein the at least one frame includes at least three frames.

25. A cell growth device for placement within a culture well, comprising:
an elongated tubular body having an opening at a first end and a second end and a lumen extending therebetween;
a ring-shaped frame supporting a cell retention member that is positioned within the elongated tubular body and which is constructed and arranged to be slidably advanced along the lumen between the first and second ends, the ring-shaped frame including a seal for engaging the elongated tubular body to prevent a flow of culture media between the ring-shaped frame and the elongated tubular body.

26. The device as defined in claim 25 wherein the ring-shaped frame includes a circumferential groove for receiving the seal.

27. The device as defined in claim 26 wherein the seal is an O-ring.

28. The device as defined in claim 25 wherein the elongated tubular body is provided with at least one support at each of the first and second ends so that the elongated tubular body can stand on either the first or the second end in the culture well.

29. The device as defined in claim 25 further comprising a plunger for advancing the ring-shaped frame along the lumen.

30. The device as defined in claim 29 wherein the plunger includes a stop that engages the elongated tubular body to limit the advancement of the ring-shaped frame along the lumen.

31. The device as defined in claim 25 wherein the elongated tubular body is standing on one of the first or second ends in the culture well.

32. The device as defined in claim 25 wherein the cell retention member includes a layer of cultured cells.

* * * * *